United States Patent [19]

Yamada et al.

[11] Patent Number: 5,047,137
[45] Date of Patent: Sep. 10, 1991

[54] SOLID ELECTROLYTE AIR/FUEL RATIO SENSOR WITH VOLTAGE CONTROL

[75] Inventors: Tetsusyo Yamada; Takao Kojima; Hiroyuki Ishiguro; Yoshihide Kami, all of Aichi, Japan

[73] Assignee: NGK Spark Plug Co., Ltd., Aichi, Japan

[21] Appl. No.: 915,839

[22] Filed: Oct. 6, 1986

[30] Foreign Application Priority Data

Oct. 5, 1985 [JP] Japan ................................ 60-222059

[51] Int. Cl.$^5$ .......................................... G01N 27/26
[52] U.S. Cl. .................................. 204/425; 204/426; 204/428
[58] Field of Search ............... 204/406, 1 S, 410, 411, 204/425, 426

[56] References Cited

U.S. PATENT DOCUMENTS

| | | | |
|---|---|---|---|
| 4,622,125 | 11/1986 | Oyama et al. | 204/406 |
| 4,622,126 | 11/1986 | Shimomura | 204/406 |
| 4,624,770 | 11/1986 | Yamada et al. | 204/425 |
| 4,702,816 | 10/1987 | Hashimoto | 204/406 |

Primary Examiner—John F. Niebling
Assistant Examiner—Bruce F. Bell
Attorney, Agent, or Firm—Sughrue, Mion, Zinn, Macpeak & Seas

[57] ABSTRACT

An air/fuel ratio sensor with a solid electrolyte oxygen pump and oxygen sensor defining a closed space therebetween. At least in the oxygen pump, porous electrodes sandwich an ionic oxygen conductive solid electrolyte. The voltage impressed on the electrodes of the pump is limited to a predetermined level, e.g., 6 V, in order to prevent blackening and cracking.

7 Claims, 5 Drawing Sheets

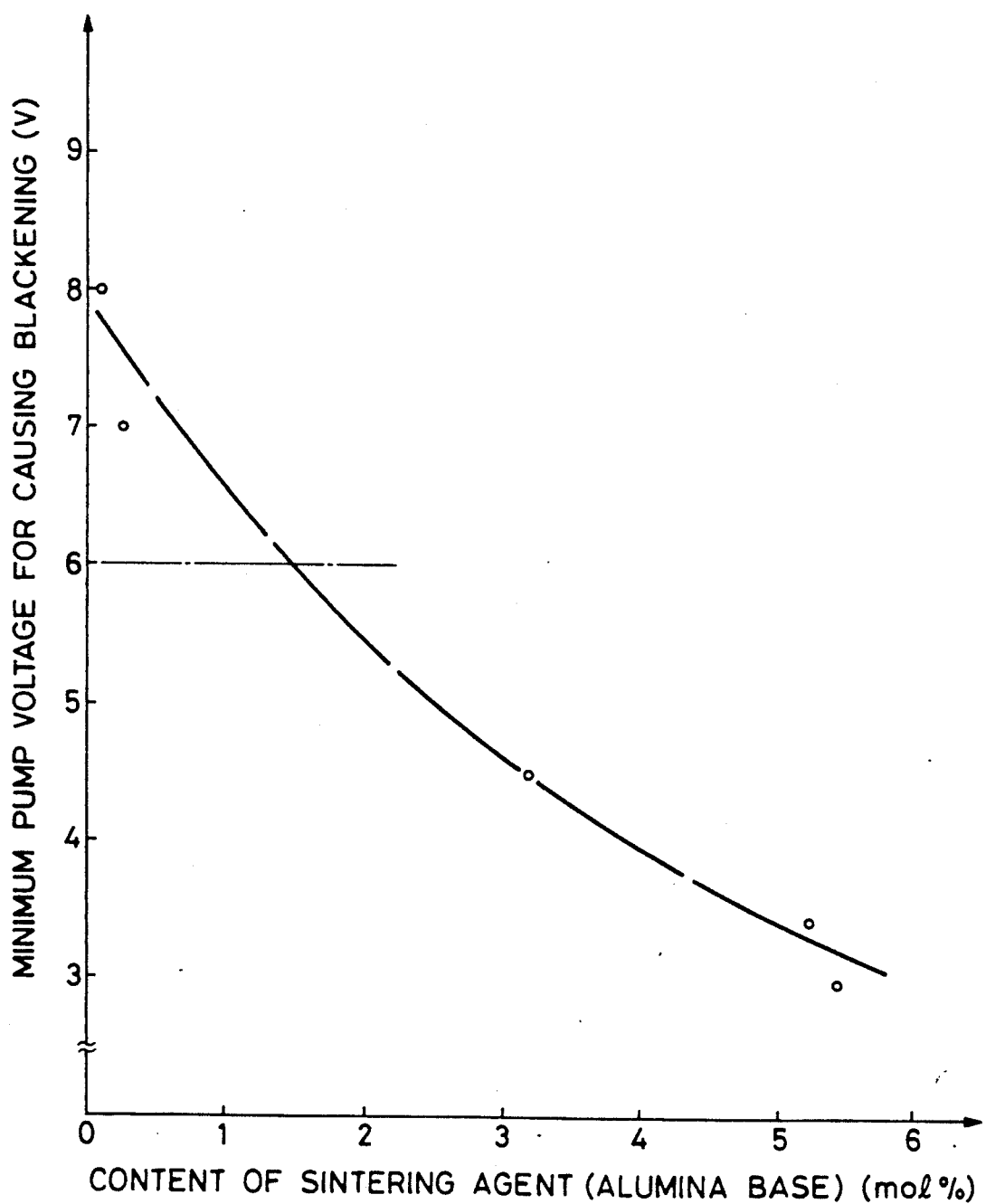

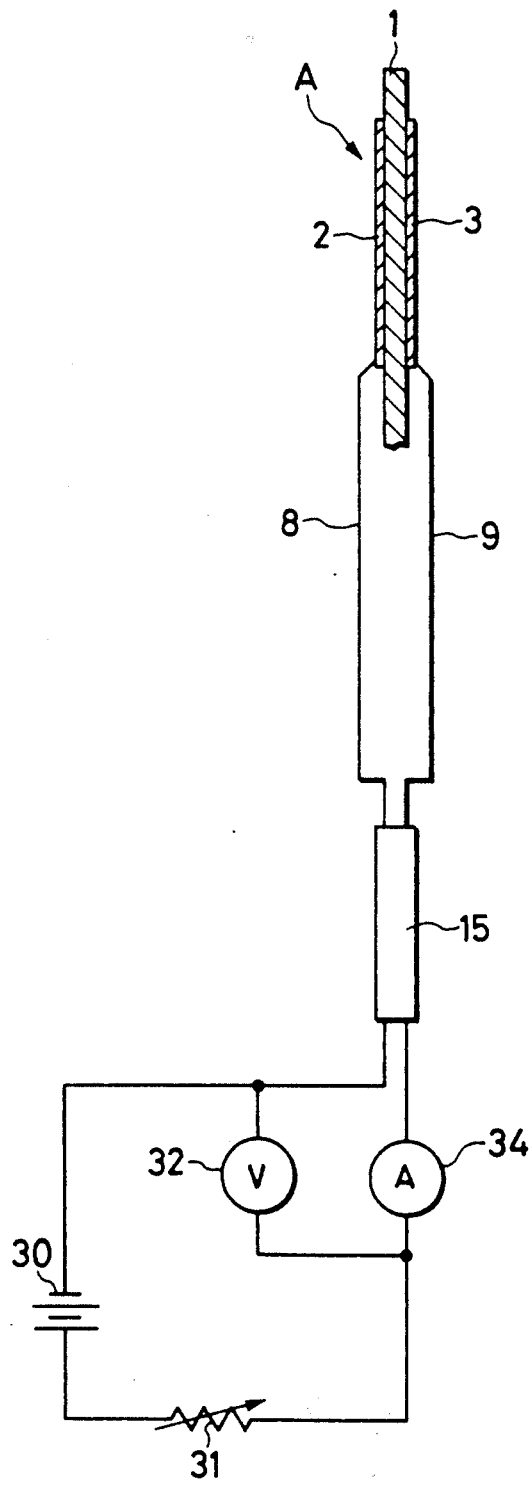
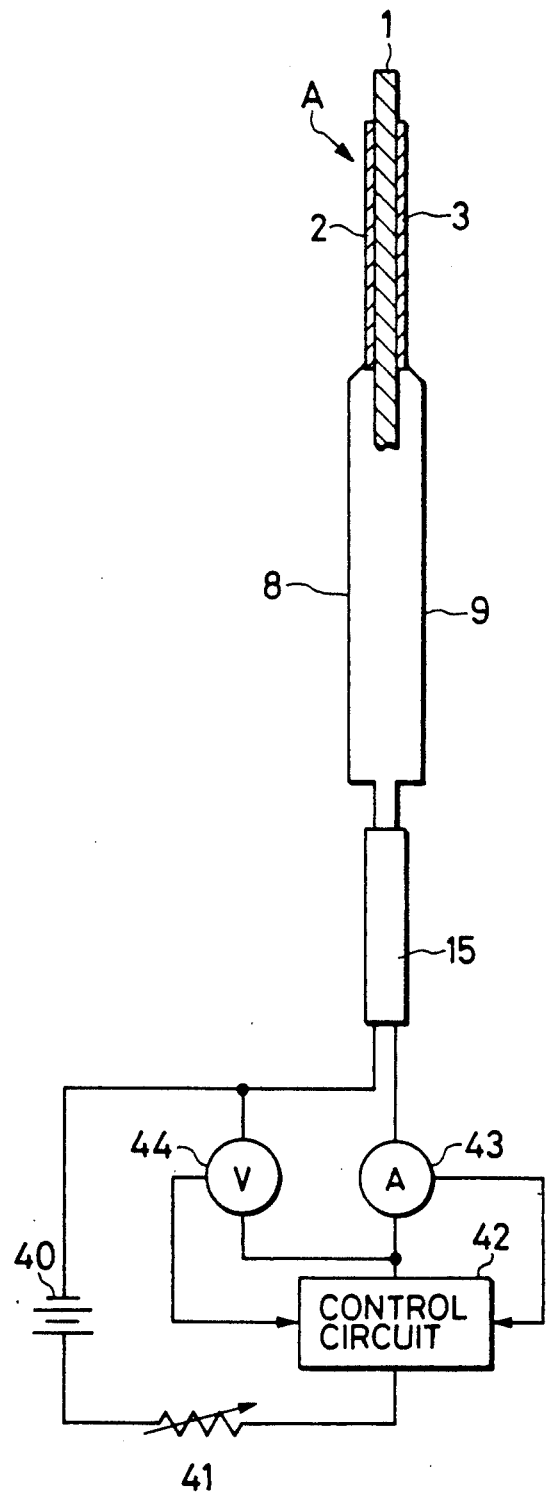

SOLID ELECTROLYTE AIR/FUEL RATIO SENSOR WITH VOLTAGE CONTROL

BACKGROUND OF THE INVENTION

1. Field of the Invention

The present invention relates to an air/fuel (A/F) ratio sensor for achieving appropriate control of combustion in internal combustion engines and other combustors by means of detecting the concentration of oxygen in the exhaust.

2. Background Art

With a view to improving fuel economy and reducing emissions, there is increasing use of automatic combustion control devices for maintaining optimum conditions of combustion in combustors, especially automotive engines. Such devices must be supplied with the necessary control information from external sources. For attaining this purpose, there have been developed various types of A/F ratio sensors which are capable of detecting the air/fuel (A/F) ratio (or excess air ratio, $\lambda$) of an air/fuel mixture by means of measuring the concentration of oxygen or inflammable components in the exhaust gas. The excess air ratio is related to the air/fuel ratio by the expression $\lambda = (A/F)/14.7$.

FIGS. 1 and 2 show the structure of a conventional A/F ratio sensor of the type which employs an oxygen concentration electrochemical cell. Since it is intended for use within an atmosphere of interest, say, the exhaust system of an automotive engine, this sensor has an oxygen pump A and an oxygen concentration electrochemical cell B, both of which have an elongated plate-like contour and which are spaced apart from each other by a small closed space a that is provided with a hole (or opening) communicating with the atmosphere of interest. The oxygen pump A and the oxygen concentration electrochemical cell B are almost alike in structure. In the device shown in FIGS. 1 and 2, a plate 1 (or 4) measuring 4 mm wide, 40 mm long and 0.7 mm thick is made of an oxygen-ion conductive solid electrolyte such as zirconium dioxide ($ZrO_2$ partially stabilized with $Y_2O_3$). Opposite sides of the tip of the plate 1 (or 4) are coated with electrode layers 2 and 3 (or 5 and 6), for example, of porous platinum formed by an appropriate thick-film deposition technique. The porous platinum is in the form of platinum paste that measures 2 mm wide, 3 mm long and about 20 micrometers thick and which has a porosity of about 30% and a binder content of 20 wt %. The electrodes 2 and 3 (or 5 and 6) are connected to lead wires 8 and 9 (or 10 and 11), respectively, and leads 8 and 11 are grounded through a terminal 14 while the leads 9 and 10 are separately led out through terminals 14 and 15.

The oxygen pump A is fed with d.c. power from a source 30 through a variable resistor 31 which is capable of regulating the current flow to the oxygen pump A. The oxygen concentration electrochemical cell B is connected via lead 10 to a voltmeter 32 for output measurement. In FIG. 1, a metal fixture 20 assists in the installation of the sensor. Various insulators 21-24 isolate the conductors. A sheath 27 facilitates the installation of the terminals. A cover 25 (FIGS. 1 and 2) protects the pump A and the cell B. A nail-shaped fin 26 is provided inwardly at a plurality of positions on the periphery of the cover 25 and serves as a hole communicating with the atmosphere of interest. A ceramic heater 7 is in a plate form. A power source 33 provides power for the heater 7 through a wiring terminal 16.

The sensor shown in FIGS. 1 and 2 is operated in the following manner. When a switch (not shown) is turned on, a constant current whose level is predetermined by the variable resistor 31 is applied from the constant-voltage d.c. supply 30 to both electrodes 2 and 3 on the oxygen pump A. The oxygen pump A then ionizes the oxygen in the atmosphere in the small closed space a (gap width=0.1 mm). The negative electrode 2 is in contact with the gap a and thus provides electrons to the oxygen. The ionized oxygen is transmitted through the tabular layer 1 of solid electrolyte toward the positive electrode 3. The oxygen ions reaching the positive electrode surface 3 are deprived of electrons and released into the atmosphere of interest as molecular oxygen. This is the pumping-out mechanism achieved by the oxygen pump A. As oxygen is removed from within the small closed space a, the oxygen in the atmosphere of interest flows into the space a by diffusion through the communication hole 26, to thereby create an equilibrium within the space a. In the space a, oxygen remains at a given concentration which is determined in accordance with the concentration of oxygen in the atmosphere of interest.

In the electrochemical cell B, one electrode surface 6 is in contact with the space a and the other electrode surface 5 is in contact with the atmosphere of interest or any atmosphere such as air having a reference oxygen partial pressure. The generated EMF is then detected and the concentration of oxygen in the atmosphere of interest is thereby detected for use as a basis for calculating the A/F ratio of that atmosphere. An optimum current value may be determined for specific conditions of use of the sensor by preliminary operational testing with the combustor.

If an A/F ratio sensor having the structure described above is used i an automotive engine, it frequently occurs that the solid electrolyte zirconium oxide 1 blackens in the vicinity of the electrode 2 on the oxygen pump A which is in contact with the small closed space a. This phenomenon called "blackening" is irreversible in that it will not disappear if it has progressed too far. The present inventors found that as blackening proceeds, the internal resistance of the oxygen pump also increases, and that if the degree of blackening increases too much, fine cracks will develop in the solid electrolyte 1 and grow in both size and number until the pump fails completely.

SUMMARY OF THE INVENTION

An object therefore, of the present invention is to provide a blackening-free A/F ratio sensor.

The above-stated object of the present invention can be attained by an A/F ratio sensor including a small closed space provided with a hole or opening communicating with an atmosphere of interest. An oxygen pump has a layer of oxygen-ion conductive solid electrolyte sandwiched between a pair of porous electrodes and thereby has a capability of pumping oxygen out of the small closed space. A power supply unit feeds electric power to the oxygen pump. The sensor further includes a power supply control circuit which stops or limits the supply of electric power to the oxygen pump when the voltage impressed on it exceeds a predetermined level.

BRIEF DESCRIPTION OF THE DRAWINGS

FIG. 4 is a graph showing the effect of a sintering agent on the minimum voltage that has to be applied to the oxygen pump in order to cause blackening.

FIG. 3 and 5 are graphs showing the results of preliminary experiments conducted in order to develop the A/F ratio sensor of the present invention, wherein FIG. 3 shows the correlation between the air excess ratio, λ, of an exhaust gas, the voltage applied to the oxygen pump, and the incidence of the occurrence of blackening in the oxygen-ion conductive solid electrolyte used in the sensor shown in FIG. 1, and FIG. 5 shows the correlation between the same factors for an apparatus of the type shown in FIG. 6;

FIG. 6 is a schematic view, with an oxygen pump being partly shown, of an experimental A/F ratio sensor that has the same construction as illustrated in FIG. 1;

FIG. 7 shows, in combination, a schematic side elevational section of the principal portion of an oxygen pump incorporated in an A/F ratio sensor of the present invention, and a diagram of a circuit for supplying electric power to the oxygen pump and a circuit for controlling the supply of power to said pump.

DETAILED DESCRIPTION OF THE PREFERRED EMBODIMENTS

A plausible mechanism for the occurrence and development of blackening is as follows. If the engine is set for a high A/F ratio, the capacity of the oxygen pump must be enhanced by increasing the power and, hence, the current to be supplied to the pump is increased. If the A/F ratio of the air/fuel mixture happens to be close to the stoichiometric value 14.7 (λ=1) at the time when the current value is switched to a higher level, the oxygen pump, which now has an increased capacity for pumping out oxygen, will exhaust most of the oxygen present in the small closed space a. At the same time, it will reduce the solid electrolyte zirconium dioxide 1 by pumping out bound oxygen present therein. Repetition of this reducing action is responsible for the progress of blackening.

The present inventors also found that there is a secondary cause of the occurrence of blackening. If the temperature of the oxygen pump A is too low, a greater energy is required for the progress of oxygen ionization at the surface of the electrode 2. Even if the supply of additional oxygen into the space a is fairly smooth, the internal resistance (impedance) of the electrode 2 on the oxygen pump A will increase to a high enough level to increase the chance of the occurrence of blackening.

The invention has been achieved on the basis of various experiments conducted in order to simulate the circumstances under which blackening has occurred in the conventional A/F ratio sensor. In order to simulate the circumstances under which the blackening of the oxygen-ion conductive solid electrolyte wound occur, the present inventors conducted the following preliminary experiments.

Figure 1:
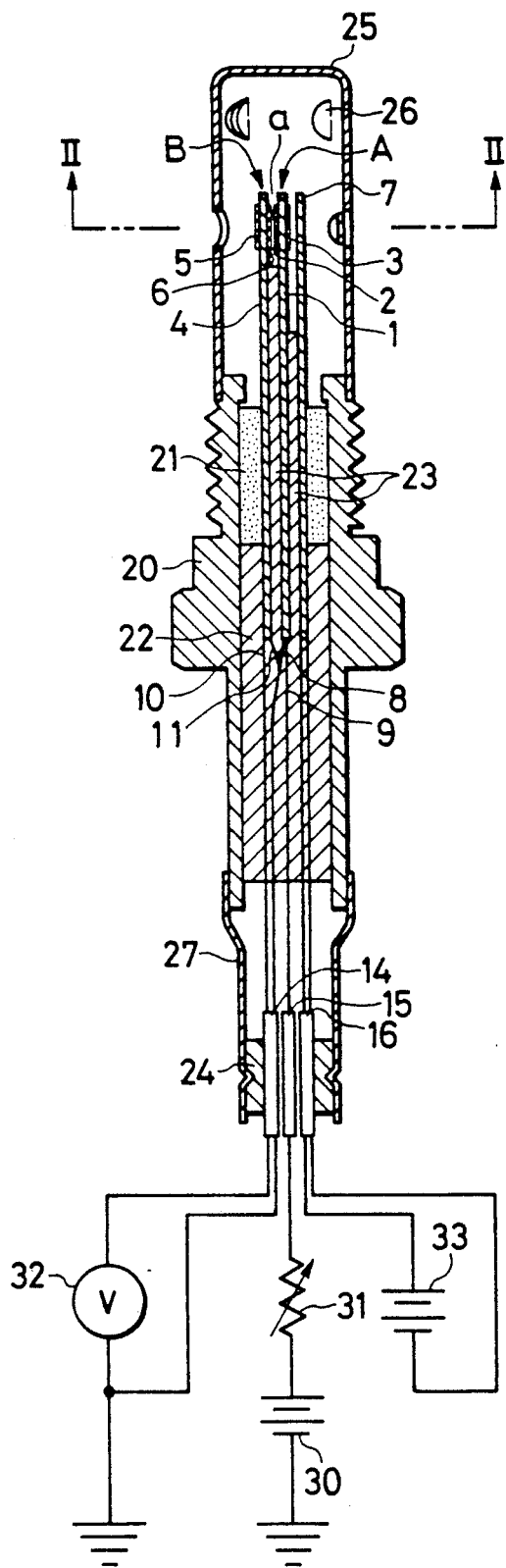
FIG. 1 shows, in combination, a side elevational section of a conventional A/F ratio sensor and a diagram for an I/O circuit therefor.

Experimental A/F ratio sensors having the same construction as depicted in FIG. 1 were exposed to exhaust gases having varying values of excess air ratio, λ. To the oxygen pump A in each sensor, varying levels of current, $I_p$, were applied for 10 minutes in order to verify the λ vs. $I_p$ profile that would cause detectable blackening. The results are shown in Table 1 below and presented graphically in FIG. 3.

TABLE 1

| λ of exhaust gas | $I_p$ (mA) | $V_p$ (V) | Blakening | $V_s$ (mV) |
|---|---|---|---|---|
| 0.9 | 28 | 6.0 | negative | 180 |
| 1.0 | 18 | 5.0 | negative | 500 |
|  | 20 | 5.5 | negative | 650 |
|  | 26 | 6.6 | positive | 760 |
| 1.2 | 30 | 5.5 | negative | 85 |
|  | 35 | 6.1 | negative | 250 |
|  | 45 | 6.7 | positive | 450 |
| 1.4 | 32 | 5.5 | negative | 55 |
|  | 37 | 6.0 | negative | 70 |
|  | 45 | 6.9 | positive | 160 |
|  | 60 | 7.2 | positive | 350 |

Figure 3:
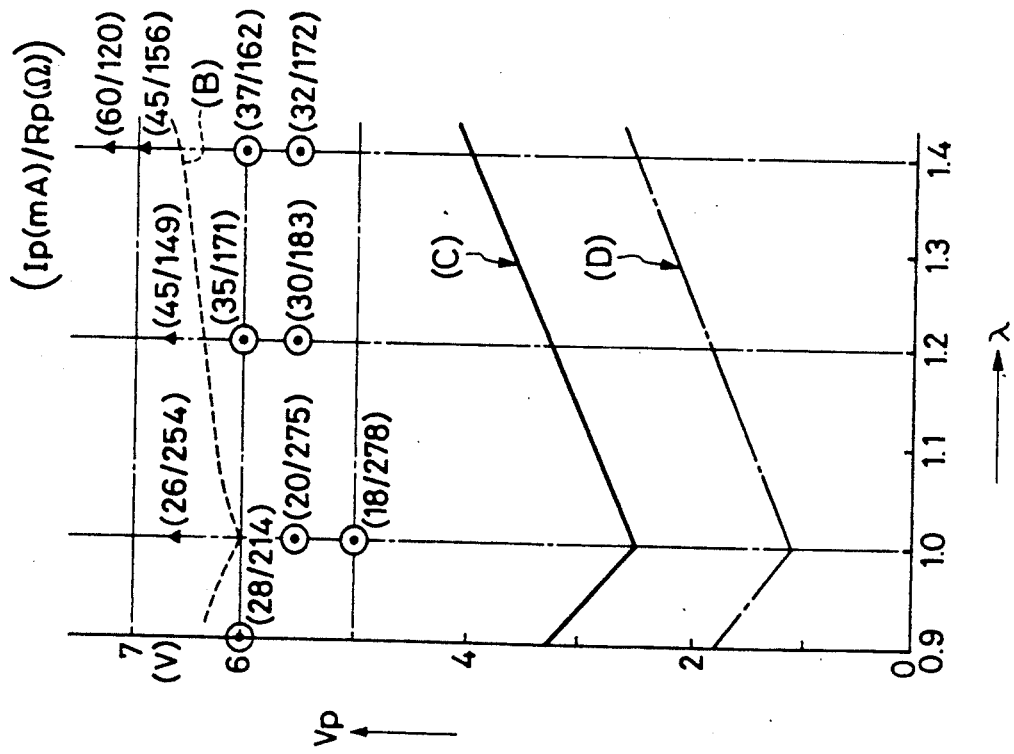

In the table and graph, λ is the excess air ratio, $I_p$ is the current flowing through the oxygen pump A, $V_p$ is the voltage impressed on the oxygen pump, and $V_s$ is the EMF generated by oxygen concentration electrochemical cell B. The numbers enclosed in parentheses in the graph are the current $I_p$ in mA and an approximate resistance $R_p$ in ohms of the oxygen pump A. In this graph $R_p = V_p/I_p$. The correct calculation for $R_p$ is discussed later. As is clear from Table 1 and FIG. 3, in the range of λ of 0.9-1.4 (13.0-20.5 in terms of the A/F ratio), blackening will never occur if the voltage $V_p$ applied to the oxygen pump A is kept at 6.0 volts or below but blackening occurs in almost all cases if $V_p$ is 6.5 volts or above. One may safely conclude that the dashed line (B) in FIG. 3 is a borderline below which blackening will not occur and above which blackening will occur. In the experiments described above, the exhaust gas was maintained at 400° C. and caused to flow at a rate of 100 liters/min., with a d.c. voltage of 10 volts being impressed on heater 7 and the oxygen pump A being held at 650° C.

The profile of voltages that had to be impressed on the oxygen pump A in order to generate a constant voltage of 40 mV in the oxygen concentration electrochemical cell B under the test conditions shown above was attained and shown by curves (C) and (D) in FIG. 3 for reference sake. Curve (C) shows the data obtained by impressing d.c. voltage of 10 volts on the heater, and curve (D) shows the data obtained by setting the heater voltage to 12.5 volts d.c.

The next topic to be discussed is the relationship between the air excess ratio, λ, in the exhaust gas and the minimum voltage that has to be impressed on the oxygen pump in order to initiate blackening. The following three reactions (1) to (3) will take place even if the air-fuel mixture is fuel-rich and the exhaust contains a negligible amount of oxygen:

$$\text{ti } C + \tfrac{1}{2}O_2 = CO \qquad (1)$$

$$H_2 + \tfrac{1}{2}O_2 = H_2O \qquad (2)$$

$$CO + \tfrac{1}{2}O_2 = CO_2 \qquad (3)$$

The equilibrium constants for these reactions, K(1) to K(3), are defined as follows:

$K(1) = PCO/PO_2^{\frac{1}{2}}$ $K(2) = PH_2O/PH_2 \cdot PO_2^{\frac{1}{2}}$ $K(3) = PCO_2/PCO \cdot PO_2^{\frac{1}{2}}$ where P is the partial pressure of the following individual gas.

Given a constant temperature and pressure, each of these constants is held at an equilibrium at the temperature prevailing in the neighborhood of the electrode surface of oxygen pump A. However, because of the action of the oxygen pump A, the following electrode reaction occurring at the negative electrode 2 will proceed to the right side so as to permit oxygen to be pumped out of the small closed space a:

$O_2 + 4e^- \rightleftharpoons 2O$.

The pumping out of oxygen will cause a decrease in $PO_2$. Therefore, in order to maintain the equilibrium constants, a dissociation reaction which proceeds to the left side of the above equation starts to take place, causing a relative increase in the amounts of rich gases in the neighborhood of the electrode. In fact, however, the exhaust gas will flow into the space a through the communicating hole, with the result that $O_2$ gas will be kept supplied with no change taking place in the partial pressures of other gaseous components in the reaction system. Experimental results show that an exhaust gas with $\lambda = 0.9$ did not cause any blackening even when $V_p$ was set to 6 volts. According to reaction equations (1) to (3), the oxygen content becomes lowest at $\lambda = 1$. This low oxygen content decreases the operating efficiency of the oxygen pump A and this would provide a favorable condition for the occurrence of blackening as a result of the increase in $V_p$. In other words, at $\lambda = 1$, the value of $V_p$ necessary to cause blackening is lower than when $\lambda$ takes other values. Therefore, the key to achieving the objects of the present invention can be attained if the upper limit for the voltage that can be impressed on the oxygen pump A without causing any blackening is determined by conducting a series of combustion experiments at $\lambda = 1$.

The present inventors also found that the value of $V_p$ is dependent not only on the type of the oxygen-ion conductive solid electrolyte, for example, zirconium oxide or yttrium oxide, used as the principal component of the oxygen pump but also on the amount of a sintering agent (e.g., alumina), as shown in FIG. 4. The term "sintering agent" referred to is a generic term. The alumina in this generic sintering agent may be replaced by other sintering agents, such as silicon, magnesia, calcia, etc. in an mount of up to about 30 mol % based on the total amount of the sintering agent. From FIG. 4, one can see that if the content of sintering agent is small, blackening will not take place even at high levels of $V_p$, while $V_p$ of 3 volts is not low enough to prevent blackening if the content of the sintering agent is high.

As already pointed out in this specification, the present inventors have learned that the chance of blackening of an oxygen-ion conductive solid electrolyte, say, zirconium oxide is also increased if the internal resistance (impedance) of the oxygen pump A exceeds a certain level. Therefore, another means for attaining the objects of the present invention is to detect the impedance, $R_p$, of the oxygen pump A and use it as information predictive of the occurrence of blackening.

An approximate value of $R_p$ can be estimated from $V_p$, the voltage impressed on the oxygen pump, and $I_p$, the current flowing through the pump. If an A/F ratio sensor of interest has the construction shown in FIG. 1 and employs a combination of an oxygen pump, an oxygen concentration electrochemical cell and a small closed space from which oxygen is to be pumped out a more precise value of $R_p$ can be attained by first subtraction $kV_s$, where k is a constant, from $V_p$, and then by dividing the difference by $I_p$. The voltage $kV_s$ is the electromotive force as determined from the output voltage, $V_s$, of the electrochemical cell by the Nernst equation. These procedures may be expressed by the following mathematical formula:

$R_p = (V_p - kV_s)/I_p$.

The calculations from the values of $V_p$ and $I_p$ that were measured in an exhaust gas atmosphere with $\lambda = 1$ which would cause the highest internal resistance of oxygen pump A provided the present inventors with sufficient evidence to conclude that the upper limit of $R_p$ for operating the A/F ratio sensor without causing any blackening of the oxygen-ion conductive solid electrolyte can safely be set at 1,500 ohms/mm², based on the electrode's surface area (for an electrode surface area of 6 mm², this value is reduced to 1,500/6 = 250 ohms).

However, it should be emphasized here that, at $\lambda$ values other than unity, $R_p$ is not a perfectly reliable indicator for blackening. In FIG. 3, $V_p$ is plotted against $\lambda$ at 11 points. The results of the simple calculation of $R_p$ from $V_p/I_p$ for the individual points are put into the parentheses beside the respective points $[I_p(mA)/R_p(ohms)]$. The values of $R_p$ would become much smaller if the formula $(V_p - kV_s)/I_p$ were used. As is clear from FIG. 3, $R_p$ in the "blackening zone" is about 254 ohms at $\lambda = 1.0$ but, at other values of $\lambda$ (1.2 and 1.4), $R_p$ becomes 149, 156 and 120. Therefore, blackening is not necessarily correlated to $R_p$ but is totally correlated to $V_p$.

Figure 5:
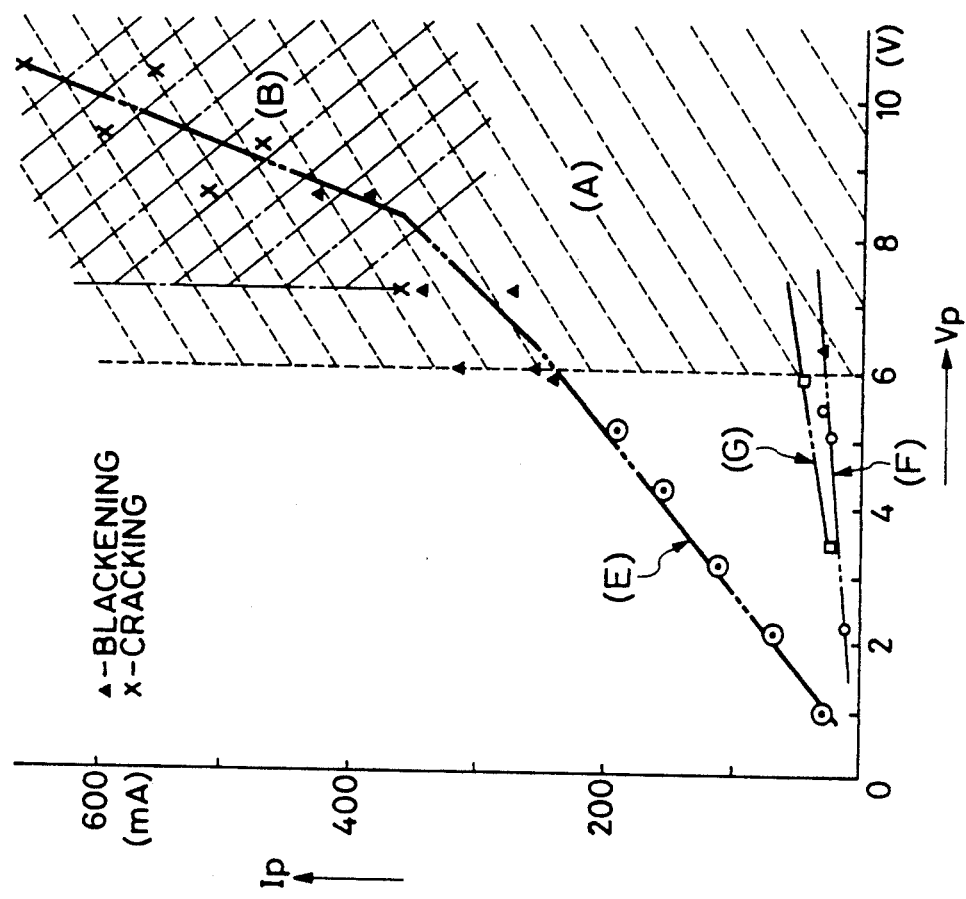

FIG. 5 shows in graphical form the $I_p$ vs. $V_p$ relationship of an A/F ratio sensor having the construction depicted in FIG. 6. The oxygen concentration electrochemical cell B and the small closed space a are omitted. This A/F ratio sensor was exposed to three kinds of atmosphere, atmospheric air, exhaust gas with $\lambda = 0.9$ and exhaust gas with $\lambda = 1.0$. In the test in the atmospheric air, the results of which are shown by curve (E) of FIG. 5, a d.c. voltage of 12.5 volts was applied to the heater 7. The combinations of $V_p$ and $I_p$ which caused blackening immediately after the voltage was impressed on the heater 7 for 10 minutes are indicated by a solid triangle, and those which caused cracking in the solid electrolyte plate 1 as a result of the progress of blackening are shown by an "X". The test conditions employed to obtain curve (E) were most favorable for the flowing of pump current $I_p$ but, as it turned out, notwithstanding sufficient heating of the oxygen pump, blackening started to take place when $V_p$ became 6 volts or higher and cracking also started to develop at 7 volts or more. Curve (F) shows the results of a test conducted in the exhaust gas with $\lambda = 1.0$, that is, the condition under which the least pump current $I_p$ could flow. In this test, the oxygen pump was heated less (10 V applied to the heater for 10 minutes). As curve (F) shows, detectable blackening started to occur when $V_p$ exceeded 6 volts. Curve (G) shows the results of a test conducted in the exhaust gas with $\lambda = 0.88$ (A/F = 13). In this test, the oxygen pump was also heated less (10 V applied to the heater for 10 minutes). Curve (G) at least shows that no detectable blackening occurred at $V_p$ of 6 volts or below. One can therefore conclude from the test results shown above that blackening will occur in the operating range of the oxygen pump indicated by single-hatching (I) in FIG. 5 and that cracking will additionally occur in the operating range indicated by double-hatching (II).

On the basis of analyses of the blackening of the oxygen-ion conductive solid electrolyte and of the results of preliminary experiments conducted to verify the validity of those analyses, the present inventors fabricated an A/F ratio sensor according to one embodiment of the present invention which has the constructional form depicted in FIG. 7. Since the sensor differs from the conventional product depicted in FIG. 1 only with respect to the provision of a circuit for controlling the supply of power to the oxygen pump A, FIG. 7 shows only a fragmentary view of the oxygen pump A plus a circuit for supplying power to this pump and a circuit for controlling the supply of power to the pump.

Figure 2:
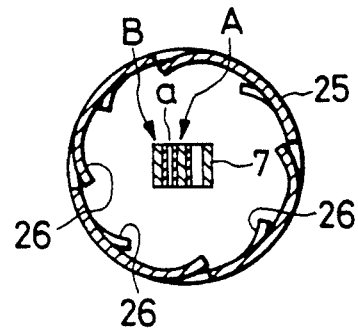
FIG. 2 is a cross section of FIG. 1 taken on line II—II.

The oxygen pump A has a known construction in that most of the end except the very tip of an elongated plate 1 of zirconium dioxide (which is one kind of oxygen-ion conductive solid electrolyte) is coated on opposite sides with porous platinum films as electrodes 2 and 3 by an appropriate thick-film deposition technique. The electrodes 2 and 3 are connected to lead wires 8 and 9, respectively. The leads are attached to a terminal 15 which also serves as an I/O terminal for the sensor. Other components are shown in FIG. 2. It is noted that some of the details of FIG. 7 also apply to electrochemical cell B. A d.c. power source 40 drives the oxygen pump A. A variable resistor 41 regulates the power to be supplied to the pump A control. A circuit 42 is provided for controlling the supply of power to the pump A. An ammeter 43 and a voltmeter 44 respectively measure $I_p$ and $V_p$. In FIG. 7, the control circuit 42, the ammeter A and the voltmeter V are shown separately but in an actual apparatus they are integrated in a single circuit unit. An embodiment of the power supply control circuit 42 is shown in FIG. 8.

Figure 8:
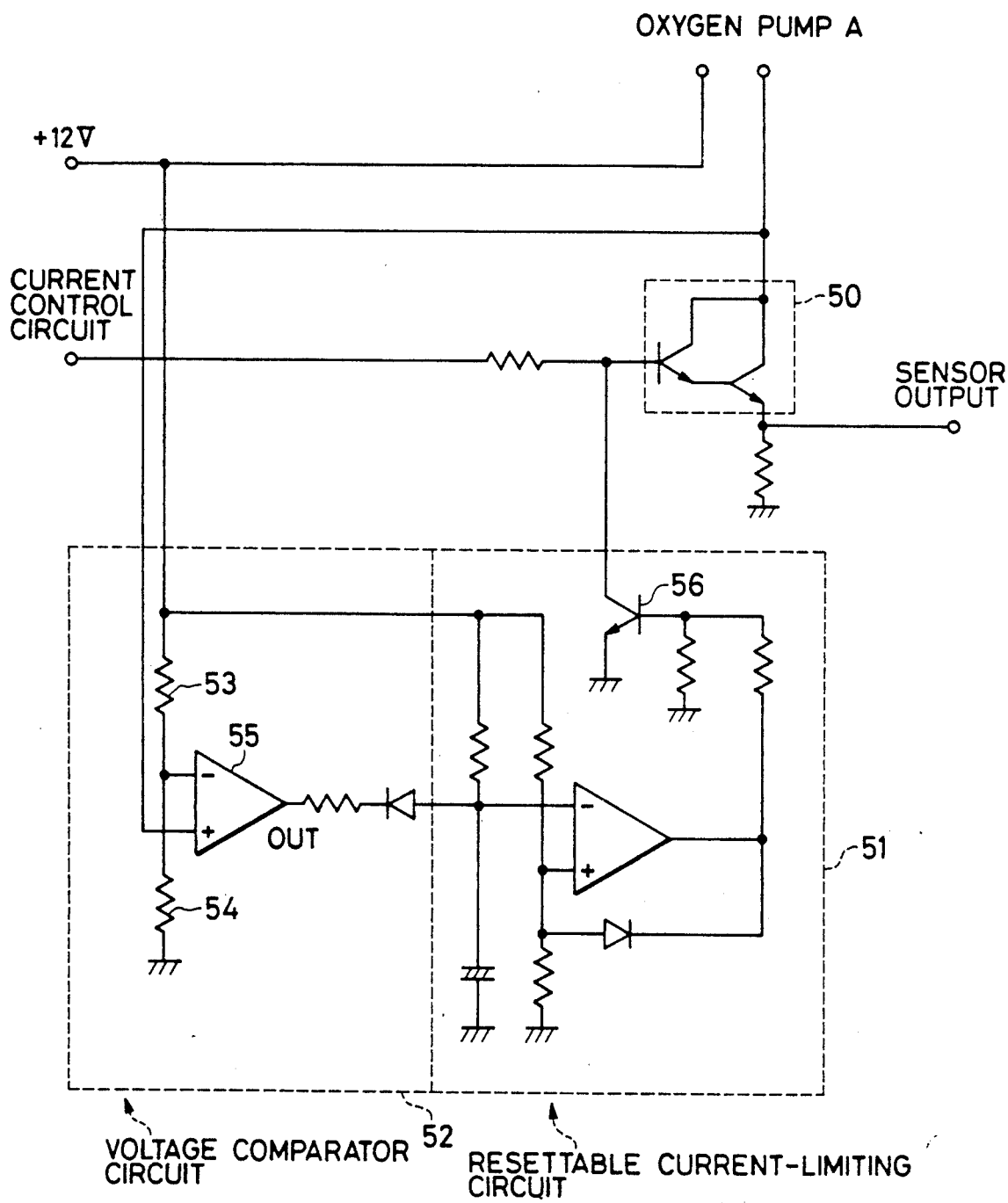
FIG. 8 is a power supply control circuit in accordance with one embodiment of the present invention.

The circuit of FIG. 8 is somewhat different from FIG. 7 in that 12 V is used as the reference potential to the pump A. The current to the pump A is usually controlled by a current control signal applied to a switch 50. However, the current control signal can be shorted by a resettable current-limiting circuit 51, itself controlled by a voltage comparator circuit 52. In the voltage comparator circuit 52, a predetermined voltage is set by resistors 53 and 54. If the variable voltage from the pump A becomes too low (i.e., the applied voltage is too high, a comparator 55 switches low, which has the effect of rendering a transistor 56 conductive. With the transistor 56 conductive, the current control signal is shorted to ground and the series switch 50 is opened, to thus interrupt the current to the pump A.

The configuration of circuit 42 may be designed in various ways in order to attain the objects of the present invention and two basic configurations are described below.

According to the first design, a circuit is provided wherein the empirically determined minimum voltage, that has to be applied to the oxygen pump in order to cause blackening in the oxygen-ion conductive solid electrolyte, is compared with an actually applied voltage which is measured with a voltmeter, and the supply of power to the oxygen pump A is stopped if the measured value of voltage exceeds the predetermined minimum level. Voltage checking may be performed throughout the operation of the oxygen pump A or, alternatively, measurement and comparison may be achieved at predetermined intervals.

The second approach is to employ two circuits, one for setting $V_{pc}$ (minimum pump voltage that causes blackening) as a function of pump current, $I_p$, and the other for comparing the set value of $V_{pc}$ with an actually measured value.

While the construction of the A/F ratio sensor of the present invention is described in the foregoing pages, it should be noted that the concept of the invention is not applicable solely to the sensor shown in FIG. 8. It is also applicable to a broad-range A/F ratio sensor where the electrode on an oxygen concentration electrochemical cell which is not in contact with the closed space is exposed to the atmospheric air or any other atmosphere that is equivalent thereto. Another A/F ratio sensor that can be operated by the concept of the present invention is one such that an oxygen pump facing a closed space is the only component (i.e., no oxygen concentration electrochemical cell is used) and that A/F ratio detection is achieved on the basis of the relationship between pump current and pump voltage.

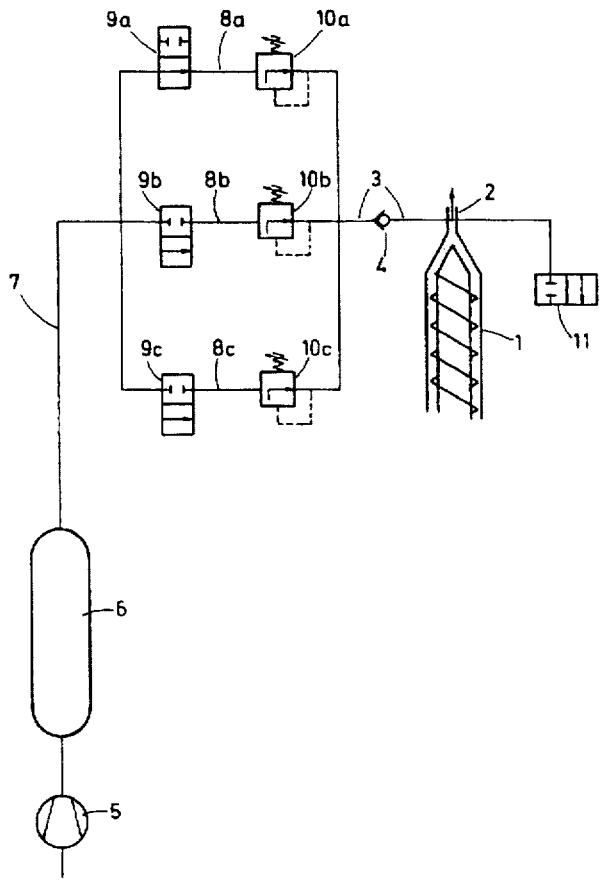

What is claimed is:

1. A blackening-free air/fuel ratio sensor, comprising:
   means for defining a closed space;
   separating means, including at lest one aperture, for separating, except through said aperature, said closed space from an atmosphere to be measured;
   an oxygen pump contained within said separating means adjacent said closed space, said pump comprising a pair of porous electrodes and a layer of oxygenion conductive solid electrolyte sandwiched therebetween;
   means for sensing a level of oxygen in said closed space;
   a power supply unit for feeding electrical power to said electrodes of said oxygen pump;
   means for sensing a voltage, impressed on said oxygen pump by said power supply unit, as information predictive of blackening of said electrolyte; and
   means for controlling said power supply unit, in response to said impressed voltage exceeding a predetermined voltage level, to avoid said blackening.

2. An air/fuel ratio sensor according to claim 1, wherein said predetermined level is approximately 5 volts or less.

3. An air/fuel ratio sensor according to claim 2, wherein said predetermined voltage level is approximately 6 volts.

4. An air/fuel sensor as recited in claim 3, wherein said solid electrolyte comprises zirconium dioxide.

5. An air/fuel sensor as recited in claim 1, wherein said controlling means controls said impressed voltage level to said predetermined voltage.

6. An air/fuel sensor as recited in claim 1, wherein said controlling means interrupts said impressed voltage.

7. An air/fuel sensor as recited in claim 1, wherein said oxygen pump and said sensing means together constitute said defining means, and said closed space is disposed therebetween.

* * * * *

UNITED STATES PATENT AND TRADEMARK OFFICE
CERTIFICATE OF CORRECTION

PATENT NO. : 5,047,137
DATED : September 10, 1991
INVENTOR(S) : YAMADA, et al

It is certified that error appears in the above-indentified patent and that said Letters Patent is hereby corrected as shown below:

Claim 2, Column 8, line 2, change "5" to --6--.

Signed and Sealed this

Twenty-sixth Day of October, 1993

Attest:

BRUCE LEHMAN

Attesting Officer

Commissioner of Patents and Trademarks

REEXAMINATION CERTIFICATE (1838th)

United States Patent [19]

Yamada et al.

[11] B1 5,047,137

[45] Certificate Issued Nov. 3, 1992

[54] SOLID ELECTROLYTE AIR/FUEL RATIO SENSOR WITH VOLTAGE CONTROL

[75] Inventors: Tetsusyo Yamada; Takao Kojima; Hiroyuki Ishiguro; Yoshihide Kami, all of Aichi, Japan

[73] Assignee: NGK Spark Plug Co., Ltd., Nagoya, Japan

Reexamination Request:
No. 90/002,533, Dec. 4, 1991

Reexamination Certificate for:
Patent No.: 5,047,137
Issued: Sep. 10, 1991
Appl. No.: 915,839
Filed: Oct. 6, 1986

[30] Foreign Application Priority Data
Oct. 5, 1985 [JP] Japan ................... 60-222059

[51] Int. Cl.⁵ ........................................... G01N 27/26
[52] U.S. Cl. ................................... 204/425; 204/426; 204/428
[58] Field of Search .................... 204/425, 426, 428

[56] References Cited
PUBLICATIONS

Shigeo Soejima and Shunzo Mase, Multi-layered Zirconia Oxygen Sensor for Lean Burn Engine Application, pp. 53–59.

*Primary Examiner*—John F. Niebling

[57] ABSTRACT

An air/fuel ratio sensor with a solid electrolyte oxygen pump and oxygen sensor defining a closed space therebetween. At least in the oxygen pump, porous electrodes sandwich an ionic oxygen conductive solid electrolyte. The voltage impressed on the electrodes of the pump is limited to a predetermined level, e.g., 6 V. in order to prevent blackening and cracking.

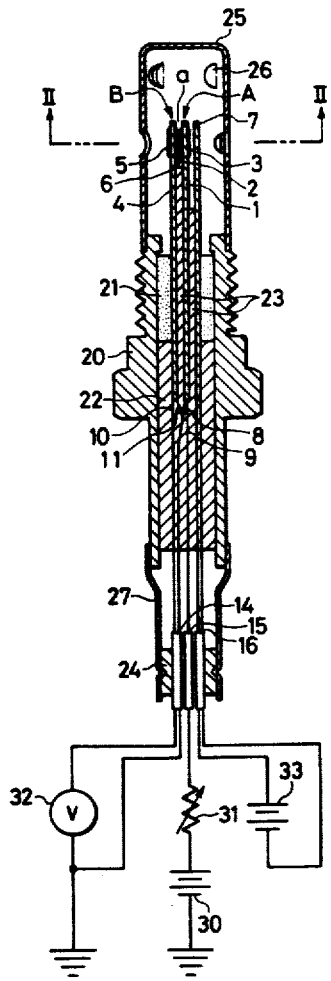

REEXAMINATION CERTIFICATE (3610th)
United States Patent [19]

Eckardt et al.

[11] B1 5,047,183

[45] Certificate Issued Aug. 25, 1998

[54] METHOD OF INJECTION MOLDING ARTICLES OF THERMOPLASTIC MATERIALS

[75] Inventors: Helmut Eckardt, Meinerzhagen; Jürgen Ehritt, Hilchenbach-Müsen, both of Germany

[73] Assignee: Battenfeld GmbH, Meinerzhagen, Germany

Reexamination Requests:
No. 90/004,706, Jun. 27, 1997
No. 90/004,857, Dec. 4, 1997

Reexamination Certificate for:
Patent No.: 5,047,183
Issued: Sep. 10, 1991
Appl. No.: 255,715
Filed: Oct. 7, 1988

[30] Foreign Application Priority Data

Oct. 9, 1987 [DE] Germany ................................ 3734164

[51] Int. Cl.⁶ .......................... B29C 45/76; B29D 22/00
[52] U.S. Cl. ............... 264/40.3; 264/328.8; 264/328.12; 264/328.13; 264/572
[58] Field of Search ........................ 264/40.3, 328.8, 264/328.12, 328.13, 572

[56] References Cited

U.S. PATENT DOCUMENTS

| | | | |
|---|---|---|---|
| 4,101,617 | 7/1978 | Friederich | 264/572 |
| 4,824,732 | 4/1989 | Hendry et al. | 264/572 X |

*Primary Examiner*—Leo B. Tentoni

[57] ABSTRACT

A method and an apparatus of injection molding articles of thermoplastic material. The method includes initially forcing molten plastics material into an injection mold in an amount sufficient for forming the article. Subsequently, a flowable medium is forced into the injection mold with a pressure which distributes the plastics material uniformly over the surface of the mold cavity of the injection mold so as to form a hollow body. The hollow body is then cooled while the pressure of the medium is maintained. Finaly, the pressure of the medium is released and the molded article is removed from the injection mold. The pressure of the medium in the mold cavity is controlled and/or varied at least temporarily until the plastics material has cooled. The apparatus for carrying out the method includes a pressure reservoir for the medium which is connectible to the injection mold through lines. The lines include control and/or regulating elements.